United States Patent [19]
Pfeiderer et al.

[11] Patent Number: 6,106,503
[45] Date of Patent: Aug. 22, 2000

[54] CATHETER VALVE

[75] Inventors: Klaus Pfeiderer, Frankfurt am Main; Peter Heise, Fuldabrück, both of Germany

[73] Assignee: CareMed Medical Produkte AG, Dresden, Germany

[21] Appl. No.: 09/064,577

[22] Filed: Apr. 22, 1998

[30] Foreign Application Priority Data

Apr. 24, 1997 [DE] Germany .................. 297 07 410 U

[51] Int. Cl.⁷ .................................................. A61M 5/00
[52] U.S. Cl. .......................... 604/246; 604/533; 604/905; 251/149.1; 251/149.6
[58] Field of Search .................................. 604/246, 247, 604/249, 256, 283, 280, 905; 251/149.1, 149.6; 137/843, 845, 847, 851, 852, 854, 857

[56] References Cited

U.S. PATENT DOCUMENTS

| | | | |
|---|---|---|---|
| 5,074,524 | 12/1991 | Wade .................................... | 251/149.1 |
| 5,353,837 | 10/1994 | Faust ....................................... | 604/249 |
| 5,360,413 | 11/1994 | Leason et al. ......................... | 604/249 |
| 5,509,433 | 4/1996 | Paradis .................................. | 251/149.1 |
| 5,520,665 | 5/1996 | Fleetwood ............................. | 604/283 |
| 5,533,983 | 7/1996 | Haining .................................. | 604/249 |
| 5,555,908 | 9/1996 | Edwards et al. ..................... | 137/329.1 |
| 5,676,346 | 10/1997 | Leinsing .............................. | 251/149.1 |
| 5,776,113 | 7/1998 | Daugherty et al. .................... | 604/280 |
| 5,839,715 | 11/1998 | Leinsing .............................. | 251/149.1 |

*Primary Examiner*—Mark O. Polutta
*Assistant Examiner*—David J. Cho
*Attorney, Agent, or Firm*—Collard & Roe, P.C.

[57] ABSTRACT

The invention relates to a catheter valve for permanently or discontinuously draining body cavities and discharging urine. The catheter valve consists of a two-component housing having a cylindrical portion and a conical portion. The conical portion houses a shaft that slides along the longitudinal axis of the housing. At a tip of the conical portion is a urine inlet opening that allows urine or other bodily fluids to flow into the catheter. At an opposite end, is a urine outlet opening that allows the fluid to flow out of the catheter. The shaft controls the flow of fluid through the catheter by selectively sealing the urine outlet opening on the catheter. In addition, a locking mechanism is provided to keep the shaft apart from the outlet valve thus allowing free flow of fluid through the catheter.

7 Claims, 2 Drawing Sheets

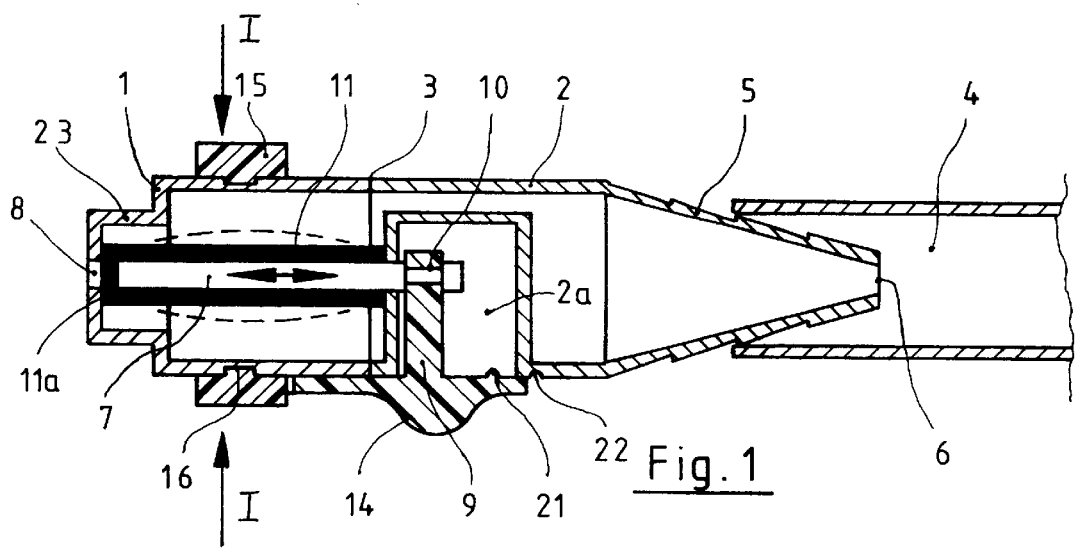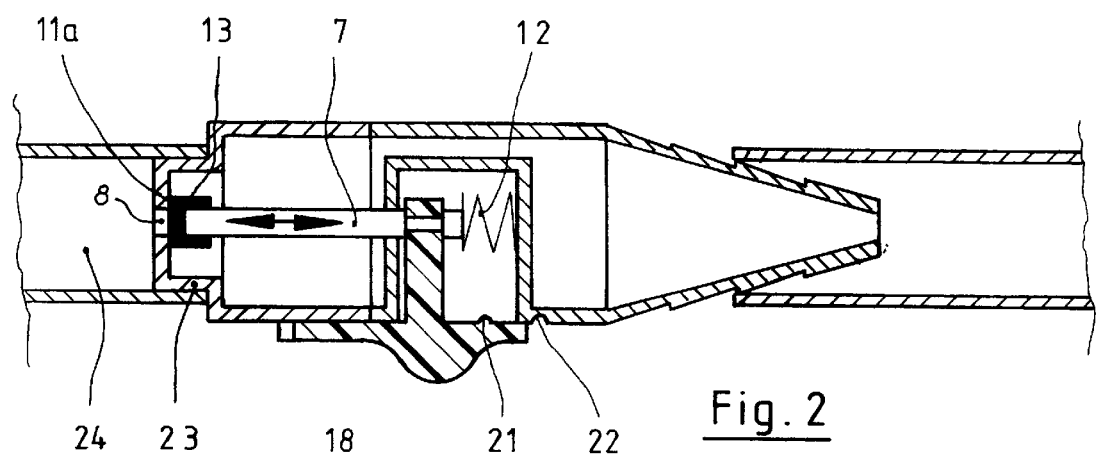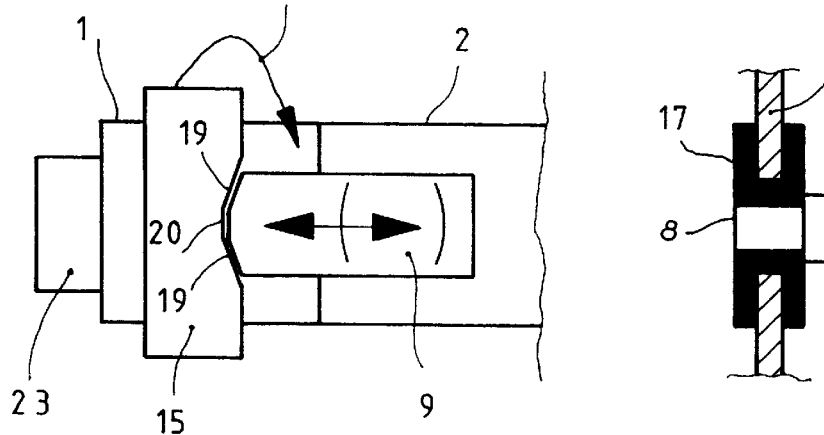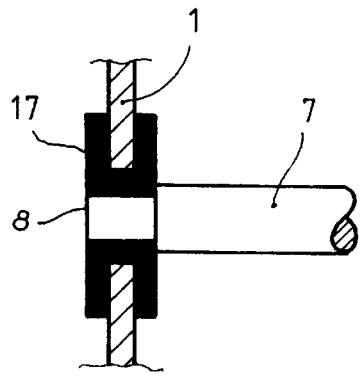

CATHETER VALVE

BACKGROUND OF THE INVENTION

1. Field of the Invention

The invention relates to a catheter valve for closing transurethral and suprapubic catheters. It may also be used as a drain valve for urine pouches. In addition, this valve is suitable for discharging other body fluids which have to be intermittently or permanently discharged via a catheter. It is also suitable for permanent urine or secretion discharge for night time use. The catheter can be used with connection of a hose and permanent opening of the catheter valve.

2. The Prior Art

The closing site of a catheter represents one of the possible inlet gates for bacteria with suprapubic or transurethral urine discharge. This site is not critical when a closed urine drainage system is connected because no disconnection is possible. In these systems, a sliding device or clamp is used in most cases with mobilized patients. However, these devices do not always assure a tight closure. The use of a simple catheter stopper may lead to problems when it is removed, because high forces are required in most cases, and small droplets or aerosols may pollute or contaminate the environment when the stopper is separated from the catheter.

To avoid these drawbacks, catheter closing devices can be made so that they can be opened and closed with relative ease and have low contamination without the above drawbacks. Therefore, the catheter can be designed so that there is a diaphragm element that kinks or squeezes together and displaces a sealing element within the zone of a valve seat. A permanently elastic force is active in all cases in the interior of the connector, with an external force counteracting this elastic force.

For example, a catheter valve shown in European Patent No. 0088871 causes a soft hose to kink through axial displacement, and interrupts the flow of urine. No permanent open position is possible for nighttime application.

With the catheter valve of the Uromed Company, a soft hose is connected by an externally actuated leaf spring and has flow-through that is intermittently interrupted. A known catheter valve of Besola AG (Switzerland) operates based on the principle of a roller clamp, as it is known from infusions. Unfortunately, the one major drawback in that the slot in which the roller clamp runs represents a dirt trap.

The three known valves specified above all suffer from the same drawback in that they are too heavy and too large, which clearly impairs the wearing comfort for the patient. The relatively large dead space between the shutoff point and the distal end of the valve leads to residual urine in the valve and to after-dripping of urine. Furthermore, the wet chamber represents an ideal environment for the growth of bacteria. In addition, these designs are very complicated which ensures costly manufacture.

Furthermore, European Patent No. 0144699B1 shows a valve that has gel cushions, spheres or other elements that are displaced in the interior of the valve body by external manual pressure. Such manual activities require great intuitive feel and, therefore, cannot be carried out in many cases by older patients.

German Patent No. 86 23 887 shows a magnetically actuated catheter valve that has a closing element that is retained in the valve housing within the valve seat by a permanent magnet that keeps the valve closed. When required, the closing element can be moved from its position by an external magnetic field to release the flow duct. This catheter valve has one drawback in that the patient must always carry a permanent magnet. Moreover, the moveable ball does not provide a flawless seal.

SUMMARY OF THE INVENTION

An object of the invention is to provide a catheter valve that has high functional safety.

It is another object of the invention is to provide a catheter valve that can be easily handled and manufactured in a simple way with favorable cost.

The problems encountered in the prior art are solved in that the catheter valve consists of a two-component housing with a urine inlet opening and a urine outlet opening. Fluid flow is controlled by a shaft. This shaft is surrounded by an elastic spring sealing element and can be moved in the axial direction against the urine outlet opening. This movement prevents urine from exiting by closing the urine outlet opening through the inherent tension of the spring sealing element. In the process, the spring sealing element is arranged at the catheter's most distal point, wherein its circular face area is pressed against the urine outlet opening. The sealing pressure is generated by the inherent tension or elasticity of the spring sealing element.

To properly handle the shaft, an ergonomically designed slide is connected with the shaft. The catheter valve can be opened for a short time by manually moving the slide against the elastic spring in the spring sealing element. In addition, the valve can be opened permanently by means of a catch mechanism arranged on the housing. The catch mechanism consists of a slide that has a ridge that locks onto the housing. The slide can be moved back and forth on the housing in an axial direction. The slide is connected with the shaft, within an open space of the housing, by clipping it onto an annular groove of the shaft.

On the other component of the housing, a rotatable ring is arranged in a groove extending over the circumference. The ring has a recess, which is engaged by the slide when the catheter valve is closed. When the slide is pushed in the axial direction on the housing, the ring is simultaneously turned on the circumference of the housing, in a radial direction. In this case, the slide is arrested in the opened condition, so that urine can continuously flow off, such as for night time use. To discharge the urine, a hose can be plugged over an attachment located on the cylindrical component of the housing, wherein the housing is connected to a collecting container.

In another embodiment of the invention a cam is arranged on the slide, and the cam engages a groove in the housing.

In another embodiment of the invention an elastic component is arranged on the shaft on the side facing the urine outlet opening.

Finally, in another embodiment of the invention there is advantageous variation has an elastic ring seal arranged in the urine outlet opening.

The invention offers a number of advantages in that the catheter valve can be designed with a relatively small size and with a light weight. This design insures a greater wearing comfort for the patient and allows for quick drainage due to an adequate cross section of flow. Any after-drip of urine is also excluded because the urine outlet opening is closed at its outermost point. The present invention permits a simple single-handed operation, which is particularly beneficial for predominantly geriatric patients. Furthermore, this design insures hygienic control of the valve to prevent infections.

BRIEF DESCRIPTION OF THE DRAWINGS

Other objects and features of the present invention become apparent from the following detailed description considered in connection with the accompanying drawings which disclose several embodiments of the present invention. It should be understood, however, that the drawings are designed for the purpose of illustration only, and not as a definition of the limits of the invention.

In the drawings, wherein similar reference characters denote similar elements throughout the several views:

FIG. 1 shows an axial cross sectional view taken through the catheter valve of the invention;

FIG. 2 shows another axial cross sectional view taken through the catheter valve with a pressure spring, and ring seal on the urine outlet opening;

FIG. 3 shows another variation on the seal of the urine outlet opening;

FIG. 4 shows a cross sectional view I—I taken through FIG. 1, with a rotatable ring.

DETAILED DESCRIPTION OF PREFERRED EMBODIMENTS

Figure 5:
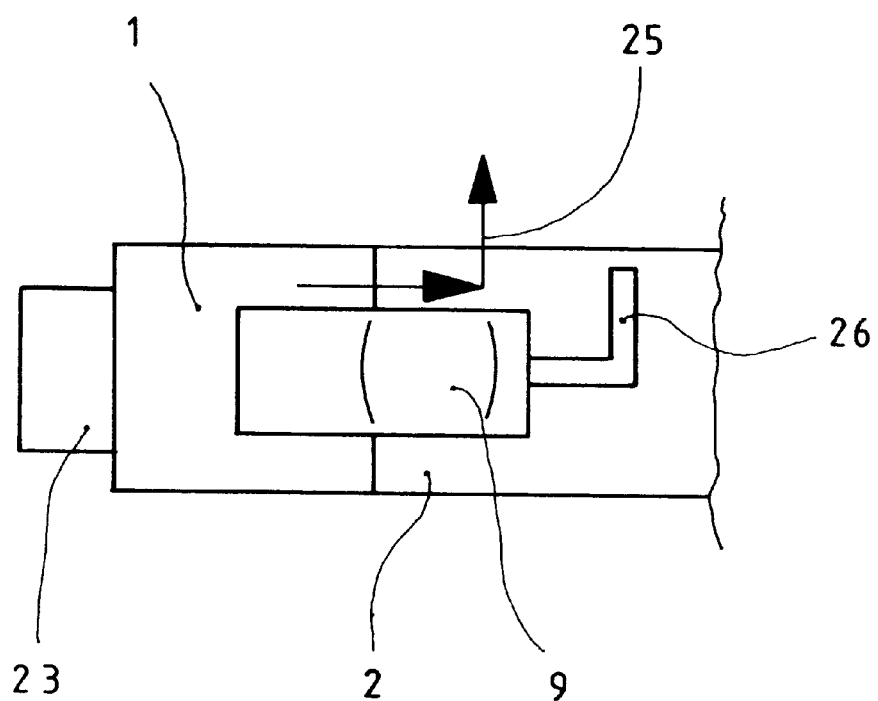
FIG. 5 shows a cross sectional view I—I taken through FIG. 1, from another embodiment using a catch mechanism.

Referring to FIG. 1 there is shown a cross sectional view of a substantially cylindrical housing component 1, having a reduced end 23 joined with a substantially conical housing component 2. These components are connected to each other along a seam 3. Conical housing component 2 is insertable into a urine discharge catheter 4. Conical surface 5 formed on the outside of conical housing component 2, may be tapered continuously or in steps. The urine discharge catheter may also lead into any body cavity to allow the discharge of fluid.

For example, urine enters the housing of the catheter valve through a urine inlet opening 6. A shaft 7 can be moved axially to determine whether the urine will flow through inlet opening 6, and leave through outlet opening 8. Shaft 7 can be axially moved using a slide 9, which is clipped to shaft 7 by means of a snap connection 10. In this process, the design of slide 9, comprising a bead 14 allows the catheter valve to be opened and closed. Bead 14 is designed to allow a user to easily move shaft 7 back and forth within housing 1. Urine outlet opening 8 is sealed by shaft 7 by means of a spring force. The spring force is generated by the elasticity of spring sealing element 11 having a butt end 11a, shown in FIG. 2. There are other ways to control the fluid flow for example, a tension spring (not shown) can be used to control the shaft. It is also possible to arrange an elastic sleeve (not shown) instead of pressure spring 12. Finally, it is also possible to use an air spring as well.

FIG. 2 shows a second embodiment of the invention where a cup shaped elastic component 13 is arranged on shaft 7. Cup shaped elastic component 13 can be pressed flush against outlet opening 8 to ensure that fluid flow is stopped. In this case, spring 12 acts as a pressure spring forcing shaft 7 into outlet opening 8.

FIG. 3 shows a third embodiment of the invention wherein an elastic ring seal 17 is provided, having a U-shaped cross section, is arranged around urine outlet opening 8. Shaft 7 has a cross sectional diameter that is larger than opening 8 so that when shaft 7 contacts opening 8 it shuts off the flow of urine through the catheter.

To allow urine to flow freely through the catheter, shaft 7 must be kept flush against pressure spring 12. As shown in FIG. 4, this occurs when a ring 15, is guided in a recess 16 (see FIG. 1) and performs a rotary movement 18 on the housing. This movement locks shaft 7 in a position corresponding with the open position of urine outlet opening 8. In addition, ring 15 contains indents 19, and flat region 20 for receiving slide 9. In the alternative, the same function can be achieved when cam 21 on slide 9 locks into groove 22.

As shown in FIG. 5 it is also possible to have a catch mechanism wherein slide 9 is locked by a pulling and turning movement 25. Slide 9 is guided into an L-shaped groove 26, thereby permanently opening a urine outlet opening 8. The instrument is closed by guiding slide 9 along L-shaped groove 26 as the turning movement takes place. To safely discharge urine, the catheter can be connected to to a collecting container via a connection hose section 24, which is pushed over an attachment 23 on housing 1. (See FIG. 2).

While several embodiments of the present invention have been shown and described, it is to be understood that many changes and modifications may be made thereunto without departing from the spirit and scope of the invention as defined in the appended claims.

What is claimed is:

1. A catheter valve comprising:
   a housing having a substantially cylindrical portion, and a substantially conical portion connected to one end of the cylindrical portion;
   at least one urine inlet opening located on said conical portion;
   at least one urine outlet opening located on said cylindrical portion;
   a displaceable shaft disposed within said housing adjacent said outlet opening wherein said shaft is displaceable along an axis within said housing to alternately open and close said at least one urine outlet opening; and
   an electric spring sealing element covering said shaft designed to seal the urine outlet opening wherein when said displaceable shaft moves axially to close said at least one urine outlet opening, said elastic spring sealing element covers said urine outlet opening to stop the flow of urine through the catheter.

2. The catheter valve according to claim 1, wherein said elastic spring sealing element is disposed on only a distal end of said shaft adjacent to said urine outlet opening in said housing.

3. The catheter valve as claimed in claim 1, further comprising an ergonomically designed slide connected to said shaft through an open space on said housing, said slide for controlling the movement of said shaft within said housing.

4. The catheter valve according to claim 1, further comprising a ring wherein when said ring is rotated radially, said ring pushes said slide along a longitudinal axis in said housing so that said shaft moves away from said urine outlet opening thus serving as a locking mechanism locking said catheter in an open position.

5. The catheter valve according to claim 1, further comprising a locking mechanism designed as a protrusion located on said slide, said protrusion for engaging a groove on said housing and locking said slide in place.

6. The catheter valve according to claim 1, further comprising an elastic component arranged on the shaft on the side facing the urine outlet opening, said elastic component for sealing said urine outlet opening and stopping the flow of urine in the housing.

7. The catheter valve according to claim 1, wherein an elastic ring seal is disposed in the urine outlet opening so that when said shaft engages said elastic ring seal, said shaft cuts off the flow of urine in the catheter.

* * * * *

UNITED STATES PATENT AND TRADEMARK OFFICE
CERTIFICATE OF CORRECTION

| | |
|---|---|
| PATENT NO. | : 6,106,503 B1 |
| APPLICATION NO. | : 09/064577 |
| DATED | : August 22, 2000 |
| INVENTOR(S) | : Pfleiderer et al. |

Page 1 of 1

It is certified that error appears in the above-identified patent and that said Letters Patent is hereby corrected as shown below:

in Column 4, line 34, (Line 13 of Claim 1), after the word "an" please change "electric" to correctly read : --elastic--.

Signed and Sealed this

Twenty-second Day of August, 2006

JON W. DUDAS
*Director of the United States Patent and Trademark Office*